United States Patent
Rees et al.

(10) Patent No.: US 10,478,081 B2
(45) Date of Patent: Nov. 19, 2019

(54) SYSTEMS AND METHOD FOR IDENTIFYING THE NEED FOR MEASUREMENT OF CARDIAC OUTPUT

(71) Applicant: Mermaid Care A/S, Nørresundby (DK)

(72) Inventors: Stephen Edward Rees, Gistrup (DK); Dan Stieper Karbing, Aalborg (DK)

(73) Assignee: Mermaid Care A/S, Nørresundby (DK)

( * ) Notice: Subject to any disclaimer, the term of this patent is extended or adjusted under 35 U.S.C. 154(b) by 207 days.

(21) Appl. No.: 15/541,795

(22) PCT Filed: Jan. 8, 2016

(86) PCT No.: PCT/DK2016/050004
§ 371 (c)(1),
(2) Date: Jul. 6, 2017

(87) PCT Pub. No.: WO2016/110297
PCT Pub. Date: Jul. 14, 2016

(65) Prior Publication Data
US 2018/0000357 A1    Jan. 4, 2018

(30) Foreign Application Priority Data
Jan. 9, 2015  (DK) ................................ 2015 70007

(51) Int. Cl.
*A61B 5/029*    (2006.01)
*G16H 50/30*    (2018.01)
(Continued)

(52) U.S. Cl.
CPC ............ *A61B 5/029* (2013.01); *A61B 5/0833* (2013.01); *A61B 5/14542* (2013.01);
(Continued)

(58) Field of Classification Search
CPC ... A61B 5/029; A61B 5/0833; A61B 5/14542; A61B 5/14551; A61B 5/7246;
(Continued)

(56) References Cited

U.S. PATENT DOCUMENTS 6,743,172 B1    6/2004  Blike
2009/0149724 A1    6/2009  Mark et al.
(Continued)

FOREIGN PATENT DOCUMENTS

| EP | 1277433 A1 | 1/2003 |
|---|---|---|
| EP | 2098163 A1 | 9/2009 |

(Continued)

OTHER PUBLICATIONS

Jansen, J. R. C. et al. "A comparison of cardiac output derived from the arterial pressure wave against thermodilution in cardiac surgery patients" British Journal of Anaesthesia 87 (2): 212-22 (2001).
(Continued)

*Primary Examiner* — Paula J Stice
(74) *Attorney, Agent, or Firm* — Dinsmore & Shohl LLP

(57) ABSTRACT

The present invention relates to a decision support system (DSS), a medical monitoring system (100), and a corresponding method for identifying the need for measurement of cardiac output (CO) based on one or more comparisons (COMP1, COMP2) in a physiological model. More specifically, for identifying when an approximated value of CO cannot be correct due to circulatory compromise and as such that another estimated or measured value of CO is required.

21 Claims, 5 Drawing Sheets

(51) Int. Cl.

| | |
|---|---|
| *G16H 50/50* | (2018.01) |
| *A61B 5/083* | (2006.01) |
| *A61B 5/145* | (2006.01) |
| *A61B 5/1455* | (2006.01) |
| *A61B 5/00* | (2006.01) |
| *G16H 50/20* | (2018.01) |
| *G16H 40/63* | (2018.01) |

(52) U.S. Cl.
CPC ........ *A61B 5/14551* (2013.01); *A61B 5/7246* (2013.01); *A61B 5/7278* (2013.01); *G16H 50/30* (2018.01); *G16H 50/50* (2018.01); *A61B 5/6852* (2013.01); *A61B 2505/03* (2013.01); *G16H 40/63* (2018.01); *G16H 50/20* (2018.01)

(58) Field of Classification Search
CPC . A61B 5/7278; A61B 5/6852; A61B 2505/03; G16H 50/50; G16H 50/30; G16H 50/20; G16H 40/63
See application file for complete search history.

(56) References Cited

U.S. PATENT DOCUMENTS

| | | | |
|---|---|---|---|
| 2013/0066174 A1 | 3/2013 | Addison et al. | |
| 2013/0218038 A1 | 8/2013 | Zhang | |
| 2014/0142970 A1 | 5/2014 | Baronov et al. | |

FOREIGN PATENT DOCUMENTS

| | | |
|---|---|---|
| WO | 9639928 A1 | 12/1996 |
| WO | 9825514 A1 | 6/1998 |
| WO | 0130234 A2 | 5/2001 |
| WO | 2004012577 A2 | 2/2004 |
| WO | 2007016056 A2 | 2/2007 |
| WO | 2009094700 A1 | 8/2009 |
| WO | 2010018542 A2 | 2/2010 |
| WO | 2010144961 A1 | 12/2010 |
| WO | 2012130249 A1 | 10/2012 |

OTHER PUBLICATIONS

Pinsky M. R., "Targets for resuscitation from shock" Minerva Anestesiol. Apr. 2003;69(4):237-44.

Oren-Grinberg A. "The PiCCO Monitor" International Anesthesiology Clinics 2010; 48(1): 57-85.

Broch O., et al. "A comparison of the Nexfin® and transcardiopulmonary thermodilution to estimate cardiac output during coronary artery surgery" Anaesthesia Apr. 2012;67(4):377-83.

Wesseling K. H., et al. "Physiocal, calibrating finger vascular physiology for Finapres" Homeostasis 1995;36:67-82.

Smith B. W. et al. "Simulation of cardiovascular system diseases by including the autonomic nervous system into a minimal model" Comput Methods Programs Biomed. May 2007;86(2):153-60.

Siggaard-Andersen O. et al., "A mathematical model of the hemoglobin-oxygen dissociation curve of human blood and of the oxygen partial pressure as a function of temperature" Clin. Chem. 30 (1984) 1646-1651.ODC.

Rees S. E. et al. "Mathematical modelling of the acid-base chemistry and oxygenation of blood: a mass balance, mass action approach including plasma and red blood cells" Eur J Appl Physiol. Feb. 2010;108(3):483-94.

Rees S. E "The Intelligent Ventilator (INVENT) project: the role of mathematical models in translating physiological knowledge into clinical practice" Comput Methods Programs Biomed. Dec. 2011;104 Suppl 1:S1-29.

McClave S. A., et al. "The use of indirect calorimetry in the intensive care unit" Curr Opin Clin Nutr Metab Care. Mar. 2013;16(2):202-8.

Karbing, D. S. et al. "Minimal model quantification of pulmonary gas exchange in intensive care patients" Medical Engineering & Physics 33 (2011) 240-248.

SYSTEMS AND METHOD FOR IDENTIFYING THE NEED FOR MEASUREMENT OF CARDIAC OUTPUT

CROSS-REFERENCE TO RELATED APPLICATIONS

This application is the U.S. National Phase of PCT/DK2016/050004 filed Jan. 8, 2016, which claims priority of Denmark Patent Application PA201570007 filed Jan. 9, 2015.

TECHNICAL FIELD OF THE INVENTION

The present invention relates to a decision support system (DSS), a medical monitoring system, and a corresponding method for identifying the need for measurement of cardiac output (CO). More specifically, for identifying when an approximated value of CO cannot be correct due to circulatory compromise and as such that another estimated or measured value is required, and that when a calculation of the minimum value of CO consistent with other values of physiological variables is required.

BACKGROUND OF THE INVENTION

Patients residing at the intensive care unit are typically monitored for their circulatory or hemodynamic status. This usually includes measurement of arterial blood pressure from either an arterial catheter or a non-invasive blood pressure cuff; and measurement of central venous pressure using a catheter. While measurement of blood pressure is a useful indication for hemodynamic status it does not provide sufficient monitoring for patients where circulation is expected to be most compromised, for example those with shock [1]. In these patients, it is often desirable to measure both pressure and the total blood flow in the circulatory system, known as the cardiac output (CO) [1]. Most clinically importance is the cardiac output from the left ventricle of a normal human being.

The reference technique for measurement of CO is using a thermodilution technique following placement of a Swan-Ganz or pulmonary artery (PA) catheter. PA catheters are placed in the pulmonary circulation via the right side of the heart, making this procedure an invasive technique. The invasive nature of the technique has led to development of a large number of less invasive techniques, ranging from thermodilution performed with catheters placed in the central vein and femoral artery [2] to measurements performed using finger cuffs [3,4]. Less invasive techniques often include a number of extra assumptions and can therefore be less accurate than using a PA catheter.

As measurement of CO can be either invasive or inaccurate and as its measurement is only crucial in patients where circulatory status is compromised, having a method to identify when it is necessary to measure CO would then be advantageous. The present invention generally relates to such systems based upon simulations performed using mathematical models of physiological processes.

SUMMARY OF THE INVENTION

Thus, an object of the present invention relates to a system and a method for assessing the need for measurement of cardiac output.

Thus, an object of the present invention relates to a system and a method for assessing the minimum value of cardiac output which is consistent with all other values of physiological variables.

Another object is the provision of integration of physiological variables in a single device for assessing the need for measurement of cardiac output and potentially also for assessing the minimum value of cardiac output consistent with other values of physiological variables. This device providing advice on the need for measurement of cardiac output and the minimum value of cardiac output in one graphical display.

In a first aspect, the present invention relates to a decision support system (DSS) for providing medical decision support for cardiac output (CO) measurements in connection with an associated patient using one or more physiological models (MOD1) implemented on a computer system, the computer system being arranged for:
  receiving first data (D1) indicative of a relative arterial oxygenation, such as SaO2, or SpO2, in the blood of the patient;
  receiving second data (D2) indicative of a haemoglobin concentration, such as Hb, in the blood of the patient;
  optionally, receiving third data (D3) indicative of an oxygen partial pressure in the arterial blood, such as PaO2, of the patient; and
  optionally, receiving fourth data (D4) indicative of a rate of oxygen consumption, such as $\dot{V}O_2$, of the patient;
the decision support system being arranged for:
  applying the physiological model(s) (MOD1) of the patient using said first data (D1), said second data (D2), optionally said third data (D3) and optionally said fourth data (D4) for modelling a tissue metabolism in the patient; A)
    i. outputting from said physiological model (MOD1), using a preliminary value for the cardiac output (CO_PREL), an estimated measure indicative of the haemoglobin oxygen saturation in the mixed venous blood of the patient (SvO2_EST); and
    ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF);
  and/or B)
    iii. outputting from said physiological model (MOD1), using a reference value for the haemoglobin oxygen saturation in the mixed venous blood of the patient (SvO2_REF), an estimated value indicative of the cardiac output (CO_EST) in the patient; and
    iv. performing a second comparison (COMP2) of said estimated value indicative for the cardiac output (CO_EST) with a reference value for the cardiac output (CO_REF) in patient; and
  based on said first comparison (COMP1, ii) and/or said second comparison (COMP2, iv) generating a measure (NM_CO) indicative of the need for an improved measurement and/or estimation of the cardiac output (CO).

The decision support system may comprise a computer system or any means for performing the steps in the present disclosure. In one embodiment, the computer system is arranged for receiving first data (D1) indicative of a relative arterial oxygenation and second data (D2) indicative of a haemoglobin concentration, but not necessarily third and fourth data (D3 and D4). In this embodiment, the computer system is correspondingly further arranged for applying the physiological model(s) (MOD1) of the patient using the first data (D1) and second data (D2), but necessarily the third and fourth data (D3 and D4), for modelling the tissue metabolism in the patient.

In another embodiment, the computer system is arranged for receiving first data (D1) indicative of a relative arterial oxygenation, second data (D2) indicative of a haemoglobin concentration, and fourth data (D4) indicative of a rate of oxygen consumption, but not necessarily third data (D3). In this embodiment, the computer system is correspondingly further arranged for applying the physiological model(s) (MOD1) of the patient using the first data (D1), the second data (D2) and the fourth data (D4), but necessarily the third data (D3), for modelling the tissue metabolism in the patient.

In another embodiment, the computer system is arranged for receiving all four abovementioned data (D1, D2, D3, D4). In this embodiment, the computer system is correspondingly further arranged for applying the physiological model(s) (MOD1) of the patient using the first data (D1), the second data (D2), the third data (D3) and the fourth data (D4) for modelling the tissue metabolism.

The decision support system (preferably comprising a computer system) may be further arranged for applying the physiological model(s) (MOD1) of the patient using said first data (D1), said second data (D2), optionally said third data (D3) and optionally said fourth data (D4) for modelling a tissue metabolism in the patient, thereby outputting an estimated measure indicative of the haemoglobin oxygen saturation in the mixed venous blood of the patient (SvO2_EST) or an estimated value indicative of the cardiac output (CO_EST) in the patient, by executing a number of steps according to a group A of steps or a group B of steps. As indicated above, group A comprises the steps of i. outputting from the physiological model(s) (MOD1), using a preliminary value for the cardiac output (CO_PREL), an estimated measure indicative of the haemoglobin oxygen saturation in the mixed venous blood of the patient (SvO2_EST); and ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF).

A second group of steps, group B, comprises the steps of:

iii. outputting from said physiological model (MOD1), using a reference value for the haemoglobin oxygen saturation in the mixed venous blood of the patient (SvO2_REF), an estimated value indicative of the cardiac output (CO_EST) in the patient; and iv. performing a second comparison (COMP2) of said estimated value indicative for the cardiac output (CO_EST) with a reference value for the cardiac output (CO_REF) in patient.

Accordingly, the step of generating a measure (NM_CO) indicative of the need for an improved measurement and/or estimation of the cardiac output (CO) may be based on either the first comparison (COMP1 of ii in A) or the second comparison (COMP2 of iv in B), or both A and B. When both groups of steps are performed, the step of generating a measure (NM_CO) indicative of the need for an improved measurement and/or estimation of the cardiac output (CO) may be based on both the first comparison (COMP1 of ii in A) and the second comparison (COMP2 of iv in B).

In one embodiment, the decision support system (DSS) provides medical decision support for cardiac output (CO) measurements in connection with an associated patient using one or more physiological models (MOD1) implemented on a computer system, the computer system being arranged for:

receiving first data (D1) indicative of a relative arterial oxygenation, such as SaO2, or SpO2, in the blood of the patient, receiving second data (D2) indicative of a haemoglobin concentration, such as Hb, in the blood of the patient, optionally, receiving third data (D3) indicative of an oxygen partial pressure in the arterial blood, such as PaO2, of the patient, and receiving fourth data (D4) indicative of a rate of oxygen consumption, such as $VO_2$, of the patient, the computer system being arranged for:

applying a physiological model (MOD1) of the patient using said first (D1), second (D2), optionally third (D3) and fourth data (D4) for modelling the tissue metabolism in the patient, i. outputting from said physiological model (MOD1), using a preliminary value for the cardiac output (CO_PREL), an estimated measure indicative of the haemoglobin oxygen saturation in the mixed venous blood of the patient (SvO2_EST), and ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF), and/or iii. outputting from said physiological model (MOD1), using a reference value for the haemoglobin oxygen saturation in the mixed venous blood of the patient (SvO2_REF), an estimated value indicative of the cardiac output (CO_EST) in the patient, and iv. performing a second comparison (COMP2) of said estimated value indicative for the cardiac output (CO_EST) with a based on said first comparison (COMP1, ii) and/or said second comparison (COMP2, iv) generating a measure (NM_CO) indicative of the need for an improved measurement and/or estimation of the cardiac output (CO).

The principle of the invention presented here is that model simulated values of mixed venous oxygen saturation can be advantageously used to assess the need for measurement of cardiac output and to assess the minimum value of cardiac output which is consistent with all other measured or simulated values. This is beneficial in evaluating the patient state and targeting measurement of cardiac output to clinical situations where standard approximation is not possible.

Thus, a system is presented where mathematical model simulations of mixed venous arterial oxygen saturation are made depending upon mathematically based physiological models and measurements including rate of oxygen consumption and an approximation of cardiac output. Depending upon the value of mixed venous oxygen saturation calculated, conclusions may be drawn as to the accuracy of the estimation of cardiac output, and consequently the need for a measurement of this value. In addition, conclusions can be drawn as to the minimum value of cardiac output which is consistent with the values of other physiological variables.

It should be noted that one, a plurality, or all of the first (D1), second (D2), third (D3), and fourth data (D4) could be measured, alternatively estimated, or more alternatively be based on model data obtained from other physiological models, cf. embodiment of FIG. 3. In one particular case, previously obtained measured data could be applied as best estimates for the data. Blood data values will normally be assumed to be for whole blood, unless otherwise stated.

It should be also noted that haemoglobin oxygen saturation in the mixed venous blood of the patient (SvO2_EST) may be equivalent to the oxygen concentration, if most of the oxygen is bound to haemoglobin.

In one embodiment, the said preliminary value for the cardiac output (CO_PREL) may be a value representative for the specific patient (P1), preferably dependent on age, gender, weight, and/or one, or more, clinical conditions having an impact on the cardiac output (CO), e.g. a standard or modified lock-up table (LUT) may be provided for the purpose.

Advantageously, said first comparison (COMP1) may comprises an evaluation of whether or not the said estimated measure indicative of the haemoglobin oxygen saturation in the mixed venous blood of the specific patient (SvO2_EST) is physiologically possible, e.g. is above, equal to, or below some known limit or reference value of the measure, and more preferably said first comparison (COMP1) comprises an evaluation of whether or not the said estimated measure indicative of the haemoglobin oxygen saturation in the mixed venous blood of the patient (SvO2_EST) is physiologically probable in view of the age, gender, weight, and/or one, or more, clinical conditions having an impact on the cardiac output (CO), and/or on the received fourth data (D4, $\dot{V}O_2$), e.g. a statistical method or computation may be applied for such as an evaluation.

In another embodiment, the said reference value for the haemoglobin oxygen saturation in the mixed venous blood of the patient (SvO2_REF, iii) may be a minimum value, preferably of 40% or 60%, more preferably 50% as is presently known to the skilled person as a reasonable minimum value for this value.

Preferably, the said reference value for the haemoglobin oxygen saturation in the mixed venous blood of the specific patient (SvO2_REF, iii) may be a value dependent on age, gender, weight, and/or one, or more, clinical conditions having an impact on the cardiac output (CO), and/or on the received fourth data (D4, $\dot{V}O_2$). Even more preferably, said second comparison (COMP2) may comprise an evaluation of whether or not said estimated value indicative for the cardiac output (CO_EST) of the specific patient is physiologically possible, e.g. is above, equal to, or below some known limits and more preferably said second comparison (COMP2) comprises an evaluation of whether or not the said estimated value indicative for the cardiac output (CO_EST) is physiologically probable in view of the age, gender, weight, and/or one, or more, clinical conditions having an impact on the estimated cardiac output (CO_EST), e.g. a statistical method or computation may be applied for such as an evaluation.

Advantageously, said measure (NM_CO) indicative of the need for an improved measurement and/or estimation of the cardiac output (CO) may be a quantitative measure, preferably a number indicating the need for an improved measurement and/or estimation of the cardiac output (CO), or a qualitative measure. The need for improved measurement may particularly be relevant for clinically purposes where the CO value is used in connection with a diagnostic application in mind i.e. for performing a diagnosis, though the present invention is not intended for a method for performing a diagnosis as such, but assisting a clinician with reliable assessment of need for an improved CO value, though the CO value itself may possibly be used as input in connection with performing a diagnosis of a patient.

In some embodiments, the first data (D1) and/or the third data (D3) may be based—wholly or partly—on a second physiological model (MOD2) of the acid-base system of the blood of the patient and/or of the interstitial fluid of the patient, cf. reference [8] for further information about such physiological models. In particular, the second physiological model (MOD2) may receive data from a third physiological model (MOD3) of the pulmonary gas exchange, the third physiological model (MOD3) further receiving data from ventilation measurements of the patient.

In other embodiments, the first data (D1), second data (D2), the third data (D3) and/or the third data (D4) may additionally be—wholly or partly—based on, or more, physiological models representing respiratory drive of patient and/or the lung mechanics of the patient.

In a second aspect, the present invention relates to a medical monitoring system capable of providing medical decision support for cardiac output (CO) measurements in connection with an associated patient using one or more physiological models (MOD1) implemented on a computer system (10), the computer system (10) being arranged for:

providing first data (D1) indicative of a relative arterial oxygenation, such as SaO2 or SpO2, in the blood of the patient, preferably by corresponding first measurement means (M1);

providing second data (D2) indicative of a haemoglobin concentration, such as Hb, in the blood of the patient, preferably by corresponding second measurement means (M2);

optionally providing third data (D3) indicative of an oxygen partial pressure in the arterial blood, such as PaO2, of the patient, preferably by corresponding third measurement means (M3); and optionally providing fourth data (D4) indicative of a rate of oxygen consumption, such as $\dot{V}O_2$, of the patient, preferably by corresponding fourth measurement means (M4);

the medical monitoring system being arranged for:
applying the physiological model (MOD1) of the patient using said first (D1), second (D2), optionally third (D3) and fourth data (D4) for modelling the tissue metabolism in the patient; A)
i. outputting from said physiological model (MOD1), using a preliminary value for the cardiac output (CO_PREL), an estimated measure indicative of the haemoglobin oxygen saturation in the mixed venous blood of the patient (SvO2_EST); and
ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF);

and/or B)
iii. outputting from said physiological model (MOD1), using a reference value for the haemoglobin oxygen saturation in the mixed venous blood of the patient (SvO2_REF), an estimated value indicative of the cardiac output (CO_EST) in the patient; and
iv. performing a second comparison (COMP2) of said estimated value indicative for the cardiac output (CO_EST) with a reference value for the cardiac output (CO_REF) in patient; and based on said first comparison (COMP1, ii) and/or said second comparison (COMP2, iv) generating a measure (NM_CO) indicative of the need for an improved measurement and/or estimation of the cardiac output (CO).

The medical monitoring system shall be construed as being implementable applying the details of the above decision support system (DSS) for providing medical decision support for cardiac output (CO) measurements in connection with an associated patient using one or more physiological models (MOD1) implemented on a computer system, including the disclosed combinations of groups A and B and the generation of a measure (NM_CO) indicative of the need for an improved measurement based on either the first comparison (COMP1 of ii in A) or the second comparison (COMP2 of iv in B) or both (COMP1, COMP2) as explained in relation to the decision support system (DSS).

In a third aspect, the present invention relates to a method for providing medical decision support for cardiac output (CO) measurements in connection with an associated patient using one or more physiological models (MOD1) implemented on a computer system, the computer system being arranged for:

receiving first data (D1) indicative of a relative arterial oxygenation, such as SaO2 or SpO2, in the blood of the patient, receiving second data (D2) indicative of a haemoglobin concentration, such as Hb, in the blood of the patient, optionally receiving third data (D3) indicative of an oxygen partial pressure in the arterial blood, such as PaO2, of the patient, and receiving fourth data (D4) indicative of a rate of oxygen consumption, such as $VO_2$, of the patient, the method comprising the steps of:

applying a physiological model (MOD1) of the patient using said first (D1), second (D2), optionally third (D3) and fourth data (D4) for modelling the tissue metabolism in the patient, i. outputting from said physiological model (MOD1), using a preliminary value for the cardiac output (CO_PREL), an estimated measure indicative of the haemoglobin oxygen saturation in the mixed venous blood of the patient (SvO2_EST), and ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF), and/or iii. outputting from said physiological model (MOD1), using a reference value for the haemoglobin oxygen saturation in the mixed venous blood of the patient (SvO2_REF), an estimated value indicative of the cardiac output (CO_EST) in the patient, and iv. performing a second comparison (COMP2) of said estimated value indicative for the cardiac output (CO_EST) with a reference value for the cardiac output (CO_REF) in patient, and generating a measure (NM_CO) indicative of the need for an improved measurement and/or estimation of the cardiac output (CO) based on said first comparison (COMP1, ii) and/or said second comparison (COMP2, iv).

The method may be carried out by means of a computer having processing means. The method may be performed according to the disclosed details apply the above details for providing medical decision support for cardiac output (CO) measurements in connection with an associated patient using one or more physiological models (MOD1) implemented on a computer system, including the disclosed combinations of groups A and B and the generation of a measure (NM_CO) indicative of the need for an improved measurement based on either the first comparison (COMP1 of ii in A) or the second comparison (COMP2 of iv in B) or both (COMP1, COMP2) as explained in relation to the decision support system (DSS).

When receiving first, second, third and/or fourth data in connection with the above method according to third aspect of the invention, it should be noted that the data could be provided from previously obtained samples and the method does not necessarily include the step(s) of obtaining the samples as such.

In a fourth aspect, the present invention relates to a computer program product being adapted to enable a computer system comprising at least one computer having data storage means in connection therewith to implement the method according to the third aspect or according to the steps and combinations disclosed in relation to the decision support system and medical monitoring system.

This aspect of the invention is particularly, but not exclusively, advantageous in that the present invention may be accomplished by a computer program product enabling a computer system to carry out the operations of the systems of the first and second aspect of the invention when down- or uploaded into the computer system. Such a computer program product may be provided on any kind of computer readable medium, or through a network.

The individual aspects of the present invention may each be combined with any of the other aspects. These and other aspects of the invention will be apparent from the following description with reference to the described embodiments.

BRIEF DESCRIPTION OF THE FIGURES

The method according to the invention will now be described in more detail with regard to the accompanying figures. The figures show one way of implementing the present invention and is not to be construed as being limiting to other possible embodiments falling within the scope of the attached claim set.

DETAILED DESCRIPTION OF THE INVENTION

Figure 1:
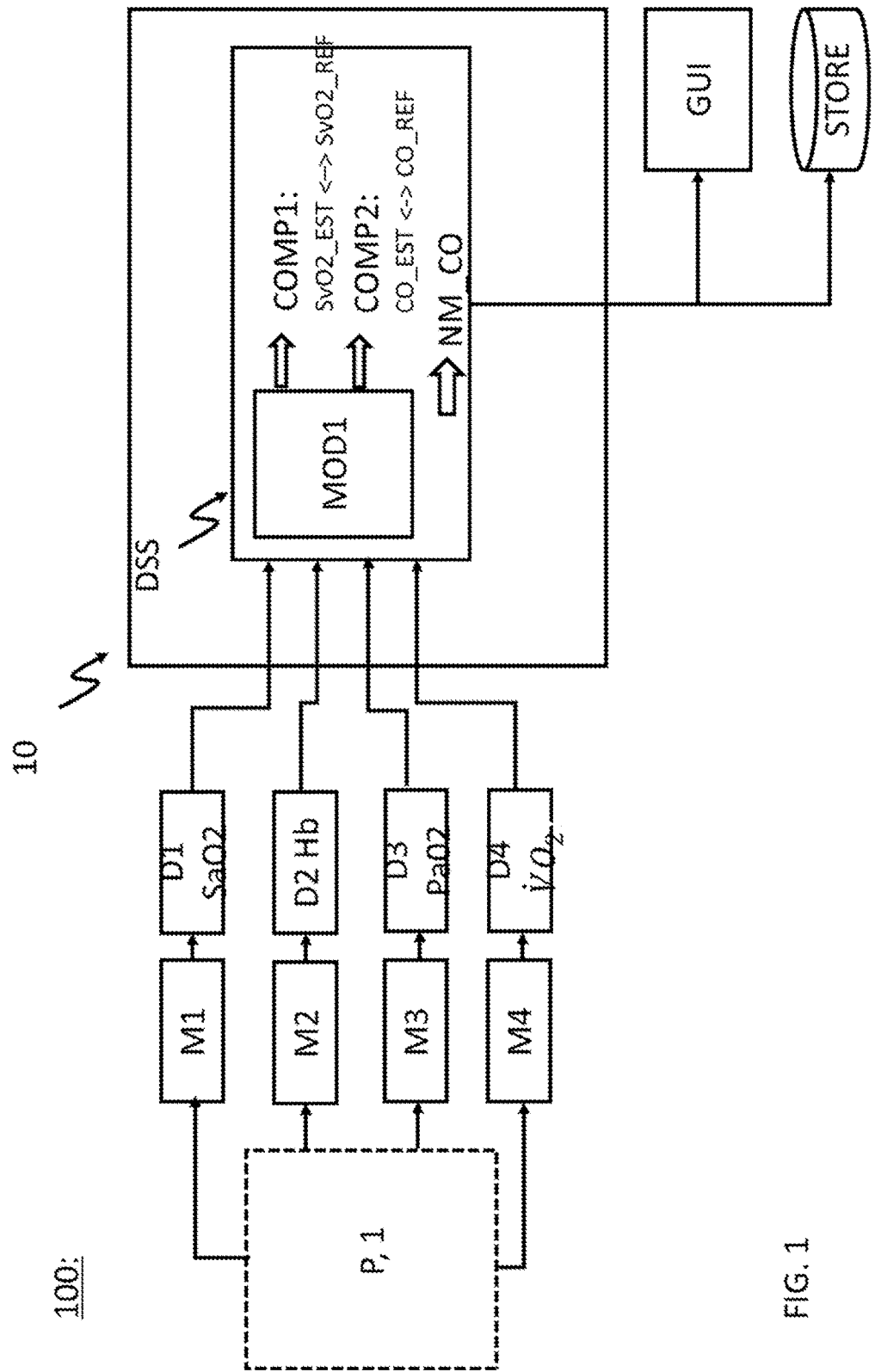
FIG. 1 is a schematic drawing of a medical monitoring system comprising a decision support system according to the present invention.

FIG. 1 is a schematic drawing of a medical monitoring system 100 comprising a decision support system DSS according to the present invention. The decision support system DSS provides medical decision support for cardiac output (CO) measurements in connection with an associated patient P,1 using a physiological models MOD1 implemented on a computer system 10.

The computer system is arranged for i.e. computationally capable of and instructed to:
  receiving first data D1 indicative of a relative arterial oxygenation, such as from measurement means M1, e.g. SaO2 or SpO2, in the blood of the patient,
  receiving second data D2 indicative of a haemoglobin concentration, such as from second measurement means M2, e.g. Hb, in the blood of the patient,
  optionally receiving third data D3 indicative of an oxygen partial pressure in the arterial blood, such as from third measurement means M3, e.g. PaO2, of the patient, and
  receiving fourth data D4 indicative of a rate of oxygen consumption, such as from fourth measurement means M4, e.g. $\dot{V}O_2$, of the patient,
the computer system being arranged for:
  applying a physiological model MOD1 of the patient using said first D1, second D2, optionally third D3 and fourth data D4 for modelling the tissue metabolism in the patient,
    i. outputting from said physiological model MOD1—using a preliminary value for the cardiac output CO_PREL, e.g. from a lock-up table—an estimated measure indicative of the haemoglobin oxygen saturation in the mixed venous blood of the patient SvO2_EST, and
    ii. performing a first comparison COMP1 of said estimated measure indicative of the haemoglobin oxygen saturation in the mixed venous blood of the patient SvO2_EST with a reference value for the haemoglobin oxygen saturation in the mixed venous blood of the patient SvO2_REF.
  Additionally or alternatively, the computer is arranged for:
    iii. outputting from said physiological model MOD1, using a reference value for the haemoglobin oxygen saturation in the mixed venous blood of the patient SvO2_REF, an estimated value indicative of the cardiac output CO_EST in the patient, and
    iv. performing a second comparison COMP2 of said estimated value indicative for the cardiac output CO_EST with a reference value for the cardiac output CO_REF in patient, and
  Finally, based on said first comparison COMP1 from step ii and/or said second comparison COMP2 from step iv there is generated a measure NM_CO indicative of the need for an improved measurement and/or estimation of the cardiac output (CO), e.g. a number indicating the need, or an outputting on a general user interface GUI a message like 'Other CO measurement/estimate needed' etc.

The invention comprises a method to assess the need for measurement of cardiac output and to assess the minimum value of cardiac output which consistent with other values of physiological variables. The principle of this invention is as follows. Model simulated or measured values of arterial blood oxygenation and acid-base status are used, along with measured tissue oxygen consumption and an estimated value of CO, to calculate mixed venous oxygen saturation ($S\bar{v}O_2$). If arterial oxygen levels are low or tissue oxygen consumption levels are high, then the simulated $S\bar{v}O_2$ values will be low. Typically, values of $S\bar{v}O_2$ or $P\bar{v}O_2$ below a minimum, say 50%, can be considered non-physiological [5]. This is due to the fact that the body typically responds to low venous oxygenation by constricting the veins, increasing flow of blood to the heart and hence increasing CO [5]. A model simulated $S\bar{v}O_2$<50% probably therefore indicates an under estimation of CO, and that a measured value of CO may be useful in interpreting the patient. In addition, if a $S\bar{v}O_2$ value of 50%, or a different arbitrary value, is considered the lowest possible value for $S\bar{v}O_2$, then it is possible to calculate the minimum value of cardiac output which is consistent with a $S\bar{v}O_2$ of 50%. For some patients the clinician may regard this as sufficient without the need for measuring CO.

This principle can be exemplified, both in terms of the models required to perform these calculations, and with examples of clinical situations where the invention may or may not result in suggestion of CO measurement or minimum values of CO.

Examples of Models Required for the Invention

Figure 2:
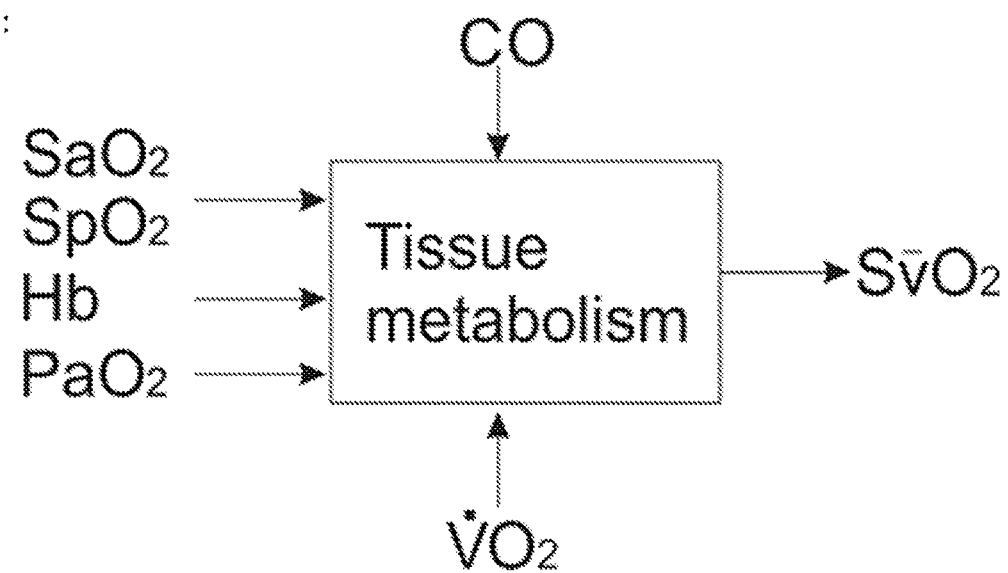
FIG. 2 is a diagram illustrating a possible simple model which could represent an embodiment of the invention.

FIG. 2 illustrates an example of a small subset of physiological models MOD1 which could be used in the method. It comprises a model component describing tissue metabolism of oxygen which enables prediction of mixed venous oxygen saturation ($S\bar{v}O_2$). This prediction can be performed using a reformulation of the well-known Fick equation to calculate oxygen concentration in the venous blood ($C\bar{v}O_2$), i.e.

$$C\bar{v}O_2 = CaO_2 - \frac{\dot{V}O_2}{CO} \qquad (1)$$

This equation calculates $C\bar{v}O_2$ from the difference between the concentration of oxygen in the arterial blood ($CaO_2$) and the ratio of oxygen consumption ($\dot{V}O_2$) and CO.

Following calculation of $C\bar{v}O_2$ it is possible to calculate $S\bar{v}O_2$ using numerical solution of the relationship between concentration ($C\bar{v}O_2$), partial pressure ($P\bar{v}O_2$) and saturation ($S\bar{v}O_2$), i.e. equation 2, and a mathematical representation of the oxygen dissociation curve, equation 3, which relates $P\bar{v}O_2$ and $S\bar{v}O_2$. For the latter, implementations of this are available in the literature [6].

$$C\bar{v}O_2 = \alpha_{O_2} P\bar{v}O_2 + S\bar{v}O_2 Hb \qquad (2)$$

$$S\bar{v}O_2 = ODC(P\bar{v}O_2, pH\bar{v}, P\bar{v}CO_2) \qquad (3)$$

In equation 2 $\alpha_{O_2}$ represents the solubility of oxygen in blood and Hb the haemoglobin concentration of blood. In equation 3, ODC represents a mathematical function of the oxygen dissociation curve, $pH\bar{v}$ is the mixed venous pH, and $P\bar{v}CO_2$ is the mixed venous partial pressure of carbon dioxide. $pH\bar{v}$, and $P\bar{v}CO_2$ can be either set to normal values or calculated for the specific patient from arterial acid-base status, measurement of tissue production of carbon dioxide ($\dot{V}CO_2$), and a mathematical model of the acid-base status of venous blood [7].

As oxygen is poorly soluble in blood, a simplification of the above process is possible if $\alpha_{O_2} P\bar{v}O_2$ is assumed to be zero. In this situation equation 3 is not required and $S\bar{v}O_2$ can be calculated directly from $C\bar{v}O_2$ using equation 2.

To solve equations 1-3 require measurement, calculation or estimation of the values of several variables. Arterial oxygen concentration can be calculated from values of arterial oxygen saturation ($SaO_2$) and arterial oxygen partial pressure $PaO_2$ using an equation analogous to equation 2 for venous blood, i.e.

$$CaO_2 = \alpha_{O_2} PaO_2 + SaO_2 Hb \qquad (4)$$

Figure 3:
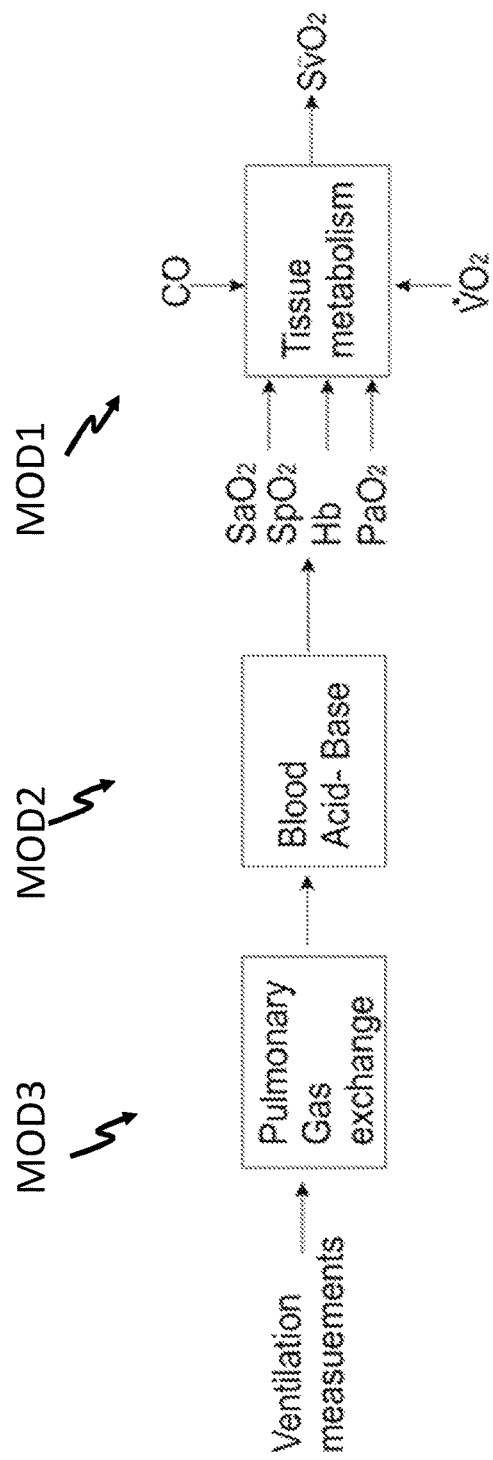
FIG. 3 is a diagram illustrating a possible more complex model which could represent an embodiment of the invention.

This requires measurement, calculation or estimation of $PaO_2$, $SaO_2$ and Hb. Hb can be obtained from laboratory values for the patient or from a blood gas analysis. $PaO_2$ and $SaO_2$ can be obtained from a blood gas analysis, i.e. the blood analysis apparatus may constitute third measurement means M3 and first measurement means M1 as schematically indicated in FIG. 1, or they can be simulated using other mathematical models. FIG. 3 illustrates a chain of previously published mathematical models which may be used to simulate arterial values of $PaO_2$ and $SaO_2$ (8). These models enable prediction of $PaO_2$ and $SaO_2$ values on changing patient state or ventilation [8]. FIG. 3 therefore represents an extended set of models which may also be used to exemplify the invention. These are exemplified in FIG. 3 with models of pulmonary gas exchange and blood acid-base chemistry, but may include mathematical representation of any physiological system required to simulate the variables necessary to calculate $S\bar{v}O_2$.

In addition as oxygen is poorly soluble in blood, if $\alpha_{O_2} PaO_2$ is assumed to be zero then measurement of $PaO_2$ is not required. The measurement of $SaO_2$ could be simplified by using a non-invasive value of $SaO_2$ obtained from a pulse oximeter ($SpO_2$), which may be considered as a particular embodiment of first measurement means M1 in FIG. 1.

$\dot{V}O_2$ can be measured at the mouth using indirect calorimetry systems [9] measuring both $O_2$ concentration and gas flow in respiratory gasses, i.e. being embodiments of the fourth measurement means M4 as schematically shown in FIG. 1. Alternatively measurement of carbon dioxide production ($\dot{V}CO_2$) could be performed at the mouth using volumetric capnography, and $\dot{V}O_2$ calculated using $\dot{V}CO_2$ and an estimate for respiratory exchange ratio (RER) or respiratory quotient (RQ).

The remaining input to calculate $S\bar{v}O_2$ in equations 1-3 is CO. As the purpose of this invention is to determine when a measurement of CO is necessary then one assume no measurement of CO is available. Indeed an available measurement would render the method redundant. An estimate of CO is therefore part of the method. CO can be estimated from standard formulae calculating an average CO depending upon a patient's ideal body weight as shown previously (10). This typically requires input of only the patient's gender and height. Any similar method for estimating CO can be applied, including estimating CO to the normal value (5 l/min) for all patients.

Following calculation of $S\bar{v}O_2$ as described above, the following steps are performed. The calculated $S\bar{v}O_2$ value is compared against a reference value, with this reference value being that assumed to be the lowest physiologically possible. Any value can be applied, but in the examples used here a value of 50% is used. If the calculated value of $S\bar{v}O_2$ is below the reference value then one or both of the following steps can be performed 1) It is indicated that the estimated value of CO is incorrect or that it may be beneficial to measure a value
2) A minimum value of CO consistent with values of other physiological values is calculated. This is done by resolving equation 2 to calculate a $C\bar{v}O_2$ consistent with $S\bar{v}O_2$ equal to the minimum (e.g. 50%), and then solving equation 1 for CO using the previous values of $CaO_2$ and $\dot{V}O_2$ plus the value of $C\bar{v}O_2$ calculated at the minimum $S\bar{v}O_2$.

EXAMPLES OF USE OF THE INVENTION

Figure 4:
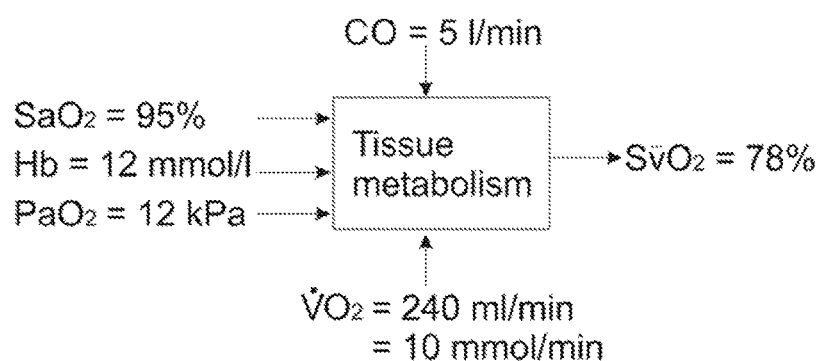
FIG. 4 shows an example of use of the method where no advice is provided to measure CO or for a minimum value of CO consistent with values of other physiological variables.

Example 1: A Situation where No Advice is Provided to Measure CO or for a Minimum Value of CO FIG. 4 illustrates a situation where no advice or minimum CO calculation would be performed. Normal values of arterial oxygenation and Hb—obtained via model simulation, estimation or measurement—combined with a normal value of CO and $\dot{V}O_2$, lead to simulation of a normal value of $S\bar{v}O_2=78\%$. There is no reason to believe that this calculation represents a poor estimate of CO, the value of $S\bar{v}O_2$ being above the minimum, and the method would neither prompt for a measured value of CO nor provide a minimum estimated value.

Figure 5:
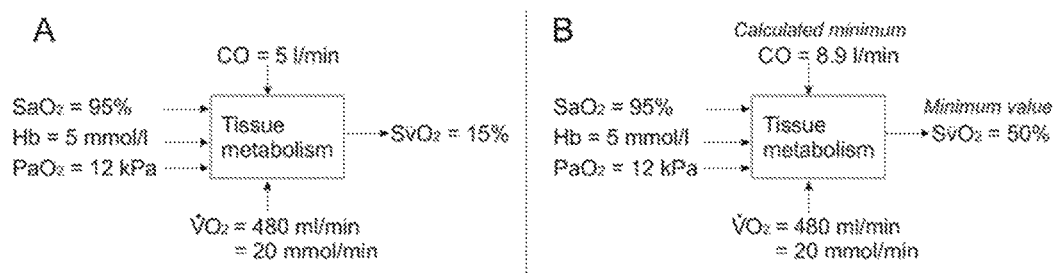
FIG. 5 shows A) an example of use of the method where advice is provided to measure CO; and B) an example of the calculation of a minimum value of CO consistent with values of other physiological variables.

Example 2: A Situation where Advice is Provided to Measure CO and a Minimum Value of CO is Calculated FIG. 5 illustrates a situation where advice to measure CO and/or a minimum CO calculation would be performed. Normal values of arterial oxygenation are input along with a value of Hb that is less than half of normal. Hb values reduced to these levels are common in patients who have received substantial fluid infusions. These are combined with a normal estimate of CO but a value of $\dot{V}O_2$ twice that normal. Such values of $\dot{V}O_2$ are consistent with increased metabolism due to muscle activity, fever or other causes. As illustrated in FIG. 5A, these values lead to simulation of an unphysiological value of $S\bar{v}O_2=15\%$, which is unlikely to be true being below the minimum value. This points to a poor estimate of CO and would therefore result in the method indicating this to the clinician and providing advice to consider measuring CO. In addition, and as illustrated in FIG. 5B, a minimum value of $S\bar{v}O_2$ approximated here as 50% could be entered into the equations. This would then result in a minimum value of CO of 8.9 l/min to be consistent with a $S\bar{v}O_2$ value of 50% or higher. This values could be accepted by the clinician if they felt it reasonable eliminating the need for CO measurement.

The overall principle of the method is then that calculation of $S\bar{v}O_2$ from an estimate of CO, values of other variables and physiological models, can indicate whether the estimate of CO is physiologically reasonable, and if not this information can be used to a) provide advice to consider measurement of CO and/or b) provide a minimum values of CO which is consistent with the values of all other physiological variables.

The invention thus relates to a method for evaluating the current estimate of CO and providing advice on the need to measure CO.

The invention also relates to a method for calculating a minimum value of CO that is consistent with other values of variables input into a physiological model.

The invention comprises measuring, estimating or simulating one or more of the following variables as use as input to the calculation of $S\bar{v}O_2$: Arterial oxygen saturation ($SaO_2$) as an example of first data D1, blood haemoglobin concentration (Hb) as an example of second data D2, arterial oxygen partial pressure ($PaO_2$) as an example of third data D3, and tissue oxygen consumption ($\dot{V}O_2$) as an example of fourth data D4.

The invention in all aspects further comprises estimating a value of CO for calculating $S\bar{v}O_2$.

The invention in all aspects further comprises analysis of these data in terms of mathematical models to calculate $S\bar{v}O_2$.

The invention in all aspects further comprises analysis of these data with a minimum value of $S\bar{v}O_2$ in terms of mathematical models to calculate a minimum CO.

The invention in all aspects may also comprise the use of one or more mathematical physiological models of pulmonary gas exchange and blood acid-base chemistry to calculate either arterial oxygenation ($SaO_2$, $PaO_2$, $CaO_2$) or to calculate $S\bar{v}O_2$.

Advantageously, the level of arterial oxygenation may be provided by measurement of arterial blood oxygen and acid-base status, by non-invasive pulse oximetry measurement ($SpO_2$), by mathematical model simulation, or other equivalent measures available to the skilled person.

Advantageously, the level tissue oxygen consumption ($\dot{V}O_2$) may be provided by measurements of oxygen fraction in respiratory gas ($FEO_2$, $PEO_2$), along with measurement of flow in the respiratory gas, or other equivalent measures available to the skilled person, cf. FIG. 3. These equivalent measures may include measurement of the level of tissue carbon dioxide production ($\dot{V}CO_2$) from measurements of carbon dioxide fraction in respiratory gas (FEC, $PECO_2$), along with measurement of flow in the respiratory gas.

Figure 6:
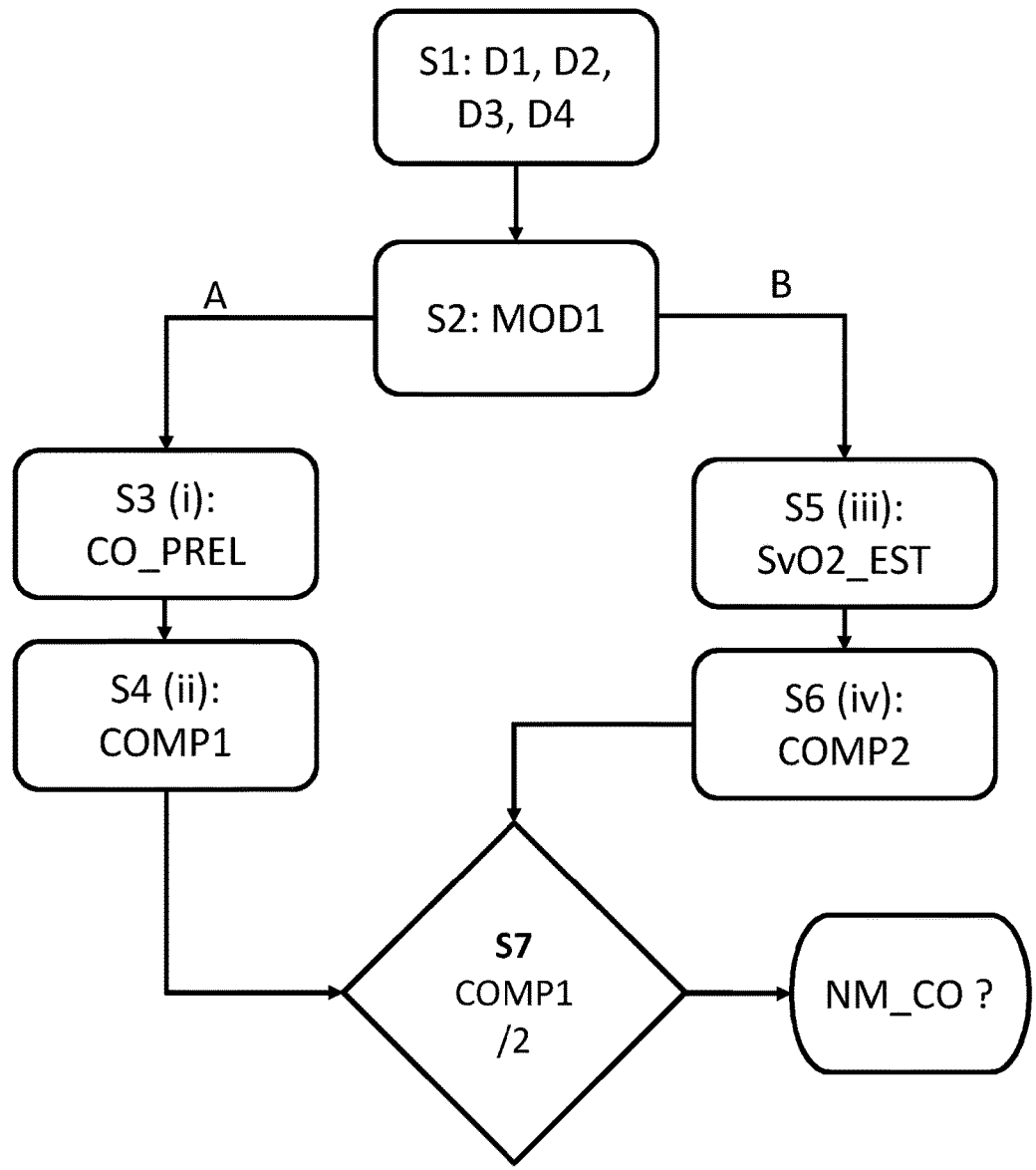
FIG. 6 shows a flow chart of the method according to the invention.

FIG. 6 shows a flow chart of the method according to the invention. The method provides medical decision support for cardiac output (CO) measurements in connection with an associated patient P,1 using a physiological model MOD1 implemented on a computer system 10,
the computer system being arranged for S1:
  first data D1 indicative of a relative arterial oxygenation, such as SaO2 or SpO2, in the blood of the patient,
  receiving second data D2 indicative of a haemoglobin concentration, such as Hb, in the blood of the patient,
  optionally receiving third data D3 indicative of an oxygen partial pressure in the arterial blood, such as PaO2, of the patient, and
  receiving fourth data D4 indicative of a rate of oxygen consumption, such as $\dot{V}O_2$, of the patient,
the method comprising:
  S2 applying a physiological model MOD1 of the patient using said first D1, second D2, optionally third D3 and fourth data D4 for modelling the tissue metabolism in the patient.
In one variant (left branch A in FIG. 6):
  i. S3 outputting from said physiological model (MOD1), using a preliminary value for the cardiac output (CO_PREL), an estimated measure indicative of the haemoglobin oxygen saturation in the mixed venous blood of the patient (SvO2_EST), and
  ii. S4 performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF),
and/or in another variant (right branch B in FIG. 6):
  iii. S5 outputting from said physiological model (MOD1), using a reference value for the haemoglobin oxygen saturation in the mixed venous blood of the patient (SvO2_REF), an estimated value indicative of the cardiac output (CO_EST) in the patient, and
  iv. S6 performing a second comparison (COMP2) of said estimated value indicative for the cardiac output (CO_EST) with a reference value for the cardiac output (CO_REF) in patient, and
    S7 generating a measure (NM_CO) indicative of the need for an improved measurement and/or estimation of the cardiac output (CO) based on said first comparison (COMP1, ii) and/or said second comparison (COMP2, iv).

The present invention may be beneficially applied when the individual is a normal person, a person under mechanical ventilation in general, including both invasive and non/invasive mechanical ventilation. In addition the invention may be beneficially applied when the patient is under continuous hemodynamic monitoring either using invasive catheter measurements or non-invasive measurements such as an inflated cuff on the arm or finger. The invention may be beneficially applied when the patient presents with, or is monitored for, circulatory abnormalities such as sepsis, heart failure or other diseases or conditions which may cause circulatory abnormalities.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs and abbreviations in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

It should be noted that embodiments and features described in the context of one of the aspects of the present invention also apply to the other aspects of the invention.

GLOSSARY

CO Blood flow leaving the heart per minute, cardiac output.
$S\bar{v}O_2$/SvO2 Haemoglobin oxygen saturation in the mixed venous blood.
$C\bar{v}O_2$ Oxygen concentration in the mixed venous blood.
$CaO_2$ Oxygen concentration in the arterial blood.
$\dot{V}O_2$ Oxygen consumption in the tissues, or oxygen flow from the blood to the tissues.
$P\bar{v}O_2$ Partial pressure of oxygen in the mixed venous blood.
$\alpha_{O_2}$ The solubility coefficient for oxygen in blood.
Hb Haemoglobin concentration in the blood.
ODC Mathematical formulation of the oxygen dissociation curve of blood.
$P\bar{v}O_2$ Partial pressure of oxygen in the mixed venous blood.
$pH\bar{v}$ pH value in the mixed venous blood.
$P\bar{v}CO_2$ Partial pressure of carbon dioxide in the blood.
$pH\bar{v}$ pH value in the mixed venous blood.
$\dot{V}CO_2$ Carbon dioxide production in the tissues, or carbon dioxide flow from the blood to the tissues.
$SaO_2$ Haemoglobin oxygen saturation in the arterial blood.
$PaO_2$ Partial pressure of oxygen in the arterial blood.
$SpO_2$ Haemoglobin oxygen saturation in the arterial blood approximated by peripheral oxygenation saturation measured using a pulse oximeter.

RER The respiratory quotient when measured using indirect calorimetry from respiratory gasses.
RQ The ratio between $\dot{V}CO_2$ and $\dot{V}O_2$
$FEO_2$ The fraction of oxygen in the expiratory gas
$PEO_2$ The partial pressure of oxygen in the expiratory gas
$FECO_2$ The fraction of carbon dioxide in the expiratory gas
$PECO_2$ The partial pressure of carbon dioxide in the expiratory gas

REFERENCES

1. Pinsky MR. Targets for resuscitation from shock. Minerva Anestesiol. 2003 April; 69(4):237-44.
Reference about the need for CO measurement in patients with sepsis and other hemodynamic conditions
2. Oren-Grinberg A. The PiCCO Monitor. International Anesthesiology Clinics 2010; 48(1): 57-85
3. Broch O, Renner J, Gruenewald M, Meybohm P, Schottler J, Caliebe A, Steinfath M, Malbrain M, Bein B. A comparison of the Nexfin® and transcardiopulmonary thermodilution to estimate cardiac output during coronary artery surgery. Anaesthesia 2012 April; 67(4):377-83
4. Wesseling K H, De Wit B, Van der Hoeven G M A, van Goudoever J, Settles, J J. Physiocal, calibrating finger vascular physiology for Finapres. Homeostasis 1995; 36:67-82
5. Smith B W, Andreassen S, Shaw G M, Jensen P L, Rees S E, Chase J G. Simulation of cardiovascular system diseases by including the autonomic nervous system into a minimal model. Comput Methods Programs Biomed. 2007 May; 86(2):153-Reference stating that Svo2 values less that 50% are unphysiological due to venoconstriction.
6. O. Siggaard-Andersen, P. D. Wimberley, I. Gothgen, M. Siggaard-Andersen, A mathematical model of the hemoglobin-oxygen dissociation curve of human blood and of the oxygen partial pressure as a function of temperature, Clin. Chem. 30 (1984) 1646-1651.ODC
7. Rees S E, Klaestrup E, Handy J, Andreassen S, Kristensen S R. Mathematical modelling of the acid-base chemistry and oxygenation of blood: a mass balance, mass action approach including plasma and red blood cells. Eur J Appl Physiol. 2010 February; 108(3):483-94.
8. Rees S E. The Intelligent Ventilator (INVENT) project: the role of mathematical models in translating physiological knowledge into clinical practice. Comput Methods Programs Biomed. 2011 December; 104 Suppl 1:S1-29
9. McClave S A, Martindale R G, Kiraly L. The use of indirect calorimetry in the intensive care unit. Curr Opin Clin Nutr Metab Care. 2013 March; 16(2):202-8 Indirect calorimetry measurements of $\dot{V}O_2$
10 Dan S. Karbing, Soren Kjargaard, Steen Andreassen, Kurt Espersen, Stephen E. Rees. Minimal model quantification of pulmonary gas exchange in intensive care patients CO calculation from ideal body weight. Medical Engineering & Physics 33 (2011) 240-248

All patent and non-patent references cited in the present application, are hereby incorporated by reference in their entirety.

The invention claimed is:
1. A decision support system (DSS) for providing medical decision support for cardiac output (CO) measurements in connection with an associated patient (P) using one or more physiological models (MOD1) implemented on a computer system, the computer system being configured for:
receiving first data (D1) indicative of an arterial oxygenation (SaO2, SpO2) in the blood of the patient;
receiving second data (D2) indicative of a haemoglobin concentration (Hb) in the blood of the patient;
the decision support system being configured for:
applying the physiological model(s) (MOD1) of the patient using said first data (D1) and said second data (D2) for modelling a tissue metabolism in the patient;
A)
i. outputting from said physiological model(s) (MOD1), using a preliminary value for a cardiac output (CO_PREL), an estimated measure indicative of haemoglobin oxygen saturation in mixed venous blood of the patient (SvO2_EST); and
ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF); and/or
B)
iii. outputting from said physiological model(s) (MOD1), using a reference value for the haemoglobin oxygen saturation in the mixed venous blood of the patient (SvO2_REF), an estimated value indicative of the cardiac output (CO_EST) in the patient; and
iv. performing a second comparison (COMP2) of said estimated value indicative for the cardiac output (CO_EST) with a reference value for the cardiac output (CO_REF) in patient; and
based on said first comparison (COMP1, step ii of A) and/or said second comparison (COMP2, step iv of B) generating a measure (NM_CO) indicative of a need for an improved measurement and/or estimation of the cardiac output (CO).
2. The decision support system (DSS) according to claim 1, the computer system being further configured for receiving third data (D3) indicative of an oxygen partial pressure in the arterial blood (PaO2) of the patient.
3. The decision support system (DSS) according to claim 1, the computer system being further ranged configured for receiving fourth data (D4) indicative of a rate of oxygen consumption ($\dot{V}O\_2$) of the patient.
4. The decision support system (DSS) according to claim 3, further configured for applying the physiological model(s) (MOD1) of the patient using said third data (D3) and/or said fourth data (D4) for modelling the tissue metabolism in the patient.
5. The decision support system (DSS) according to claim 1, wherein said preliminary value for the cardiac output (CO_PREL) is a value representative for a specific patient (P1), dependent on age, gender, weight, and/or one, or more, clinical conditions having an impact on the cardiac output (CO).
6. The decision support system (DSS) according to claim 1, wherein said first comparison (COMP1) comprises an evaluation of whether or not the said estimated measure indicative of the haemoglobin oxygen saturation in the mixed venous blood of the specific patient (SvO2_EST) is physiologically possible.
7. The decision support system (DSS) according to claim 1, wherein the said reference value for the haemoglobin oxygen saturation in the mixed venous blood of the patient (SvO2_REF, iii) is a minimum value, of 40% or 60%, or of 50%.
8. The decision support system (DSS) according to claim 1, wherein the said reference value for the haemoglobin oxygen saturation in the mixed venous blood of the specific patient (SvO2_REF, iii) is a value dependent on age, gender, weight, and/or one, or more, clinical conditions having an impact on the cardiac output (CO), and/or on the received fourth data (D4, $\dot{V}O\_2$).

9. The decision support system (DSS) according to claim 8, wherein said second comparison (COMP2) comprises an evaluation of whether or not said estimated value indicative for the cardiac output (CO_EST) of the specific patient is physiologically possible.

10. The decision support system (DSS) according to claim 1, wherein said measure (NM_CO) indicative of the need for an improved measurement and/or estimation of the cardiac output (CO) is a quantitative measure, the quantitative measure being a number indicating the need for an improved measurement and/or estimation of the cardiac output (CO), or an qualitative measure.

11. The decision support system (DSS) according to claim 1, wherein the first data (D1) and/or the third data (D3) is based, wholly or partly, on a second physiological model (MOD2) of an acid-base system of the blood of the patient and/or of an interstitial fluid of the patient.

12. The decision support system (DSS) according to claim 11, wherein the second physiological model (MOD2) receives data from a third physiological model (MOD3) of a pulmonary gas exchange, the third physiological model (MOD3) receiving data from ventilation measurements of the patient (P).

13. The decision support system (DSS) according to claim 1, wherein the first data (D1), the second data (D2), the third data (D3) and/or the third data (D4) is additionally based, wholly or partly, on, one or more, physiological models representing respiratory drive of patient and/or lung mechanics of the patient.

14. A medical monitoring system capable of providing medical decision support for cardiac output (CO) measurements in connection with an associated patient (P,1) using one or more physiological models (MOD1) implemented on a computer system, the computer system being configured for:
  providing first data (D1) indicative of an arterial oxygenation (SaO2, SpO2) in the blood of the patient, by corresponding first measurement means (M);
  providing second data (D2) indicative of a haemoglobin concentration (Hb) in the blood of the patient, by corresponding second measurement means (M2);
  the medical monitoring system being configured for:
    applying the physiological model(s) (MOD1) of the patient using said first data (D1) and said second data (D2) for modelling a tissue metabolism in the patient;
  A)
    i. outputting from said physiological model (MOD1), using a preliminary value for the cardiac output (CO_PREL), an estimated measure indicative of the haemoglobin oxygen saturation in mixed venous blood of the patient (SvO2_EST); and
    ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF); and/or
  B)
    iii. outputting from said physiological model (MOD1), using a reference value for the haemoglobin oxygen saturation in the mixed venous blood of the patient (SvO2_REF), an estimated value indicative of the cardiac output (CO_EST) in the patient; and
    iv. performing a second comparison (COMP2) of said estimated value indicative for the cardiac output (CO_EST) with a reference value for the cardiac output (CO_REF) in patient; and
    based on said first comparison (COMP1, step ii of A) and/or said second comparison (COMP2, step iv of B) generating a measure (NM_CO) indicative of a need for an improved measurement and/or estimation of the cardiac output (CO).

15. The medical monitoring system according to claim 14, the computer system being further configured for providing third data (D3) indicative of an oxygen partial pressure in the arterial blood (PaO2) of the patient, by corresponding third measurement means (M3).

16. The medical monitoring system according to claim 15, the computer system being further configured for providing fourth data (D4) indicative of a rate of oxygen consumption ($\dot{V}O\_2$) of the patient, by corresponding fourth measurement means (M4).

17. The medical monitoring system according to claim 16, further configured for applying the physiological model(s) (MOD1) of the patient using said third data (D3) and/or said fourth data (D4) for modelling the tissue metabolism in the patient.

18. A method for providing medical decision support for cardiac output (CO) measurements in connection with a patient (P,1) using one or more physiological models (MOD1) implemented on a computer system, the computer system being configured for:
  receiving first data (D1) indicative of an arterial oxygenation (SaO2, SpO2) in the blood of the patient;
  receiving second data indicative of a haemoglobin concentration (Hb) in the blood of the patient;
  the method comprising the steps of:
    applying the physiological model(s) (MOD1) of the patient using said first data (D1), said second data (D2) for modelling a tissue metabolism in the patient;
  A)
    i. outputting from said physiological model (MOD1), using a preliminary value for the cardiac output (CO_PREL), an estimated measure indicative of a haemoglobin oxygen saturation in mixed venous blood of patient (SvO2_EST); and
    ii. performing a first comparison (COMP1) of said estimated measure indicative of the haemoglobin oxygen saturation in the mixed venous blood of the patient (SvO2_EST) with a reference value for the haemoglobin oxygen saturation in the mixed venous blood of the patient (SvO2_REF); and/or
  B)
    iii. outputting from said physiological model (MOD1), using a reference value for the haemoglobin oxygen saturation in the mixed venous blood of the patient (SvO2_REF), an estimated value indicative of the cardiac output (CO_EST) in the patient; and
    iv. performing a second comparison (COMP2) of said estimated value indicative for the cardiac output (CO_EST) with a reference value for the cardiac output (CO_REF) in the patient; and
    generating a measure (NM_CO) indicative of a need for an improved measurement and/or estimation of the cardiac output (CO) based on said first comparison (COMP1, step ii of A) and/or said second comparison (COMP2, step iv of B).

19. The method according to claim 18, the computer system being further configured for receiving third data (D3) indicative of an oxygen partial pressure in the arterial blood (PaO2) of the patient.

20. The method according to claim 19, the computer system being further configured for receiving fourth data (D4) indicative of a rate of oxygen consumption ($\dot{V}O\_2$) of the patient.

21. The method according to claim 20, further comprising the step of applying the physiological model(s) (MOD1) of the patient using said third data (D3) and/or said fourth data (D4) for modelling the tissue metabolism in the patient.

* * * * *